United States Patent [19]

Dawson

[11] 4,107,983
[45] Aug. 22, 1978

[54] METHOD AND MACHINE FOR DETECTING AND CORRECTING TENSION OF SAW BLADES

[75] Inventor: Chester H. Dawson, Danbury, Conn.
[73] Assignee: Remington Arms Company, Inc., Bridgeport, Conn.
[21] Appl. No.: 822,418
[22] Filed: Aug. 8, 1977
[51] Int. Cl.² .......................................... G01N 3/20
[52] U.S. Cl. ................................................ 73/100
[58] Field of Search ............... 73/100, 104, 105, 144; 72/87

[56] References Cited

U.S. PATENT DOCUMENTS

| 3,916,680 | 11/1975 | Allen et al. | 73/100 |
| 4,027,531 | 6/1977 | Dawson | 73/100 |

*Primary Examiner*—Anthony V. Ciarlante
*Attorney, Agent, or Firm*—William L. Ericson; Nicholas Skovran

[57] ABSTRACT

A method for detecting the local and overall distribution of tension in saw blades involves elastically deflecting a properly-tensioned model blade, which is loose in the center, into a compound curvature in the form of a saddle, and adjusting the amount of deflection until the blade surface becomes flat and rectilinear along one of two perpendicular axes of the deflection. Any similar blade of unknown tension which is to be treated is then subjected to the same deflection, and inspected for rectilinearity along the same axis of deflection. Any regions projecting from this axis contain excess tension, and are designated for hammering to loosen them. The blade is rotated while the deflection axes remain stationary, so that the local and overall tension levels in the entire blade may be conformed to those of the model blade.

7 Claims, 5 Drawing Figures

METHOD AND MACHINE FOR DETECTING AND CORRECTING TENSION OF SAW BLADES

BACKGROUND OF THE INVENTION

This invention relates to saw straightening and tensioning, and more specifically to a novel method and machine for detecting and correcting tension defects in a circular saw blade, and providing a proper distribution of tension so that the blade will run straight and true at cutting speeds.

A thorough discussion of the problems involved in tensioning saw blades appears in my prior U.S. Pat. Nos. 3,964,348 issued June 22, 1976, and 4,027,531 and issued June 7, 1977. Those patents generally disclose and claim a method of detecting and correcting tension levels in a saw blade by elastically bowing the blade toward a curved locus having a contour to which the blade would fully conform if it were properly tensioned and straightened. The method then involves sensing deviations of the blade surface from the proper curved locus.

The preferred practice is to bow the blade into the approximate form of a segment of a right-circular cylinder, that is, to bow it around an axis parallel to a diameter of the blade but spaced apart along the major rotational axis of the blade from its surface. This is done by pressing axially at the center of the blade in one axial direction, while pressing in the opposite axial direction at two points near diametrally opposite edges of the blade and aligned on a common diameter. The resulting curvature takes place in a family of planes parallel to a plane defined by this common diameter and the rotational axis of the blade; while there is no substantial curvature in perpendicular planes parallel to the rotational axis of the blade.

Detection of the resulting curvature is therefore carried out along a curved path, which at least approximately lies in a plane defined by the common diameter of pressure application and the rotational axis. This method is effective and satisfactory, but does require a relatively sophisticated and well-adjusted mechanism capable of sweeping the sensor accurately through the proper curved path. Since the proper curvature is altered by a change in any of several parameters, including blade diameter, thickness, material, and desired overall tension distribution, careful readjustment is called for when batches of different blades with different specifications are to be processed.

BRIEF DESCRIPTION OF THE INVENTION

The present invention is based on my discovery that, by elastically deflecting a properly-tensioned saw blade into the complex form of a saddle, while supporting it in a horizontal position, a condition of specific deflections may be attained in which one particular axis of the properly-tensioned blade will be rectilinear or flat; and further, that the region of this particular axis may be used as a detecting location for determining, relative to a properly-tensioned blade, the local and overall tension distribution in any selected similar blade which is to be treated.

The implication of this discovery is that a position detector may be moved in a flat plane to sense the location of the blade surface, rather than in a specific curved path. I take advantage of this fact to carry out the general objects of my invention, which are to simplify the detection and correction of local and overall tension levels in saw blades, and to provide a novel method and machine for this purpose. The advantages of the invention include more rapid conversion for treatment of saw blades of different specifications, and a less complex and expensive machine structure. Further objects and advantages will appear as the following description proceeds.

Briefly stated, according to a preferred embodiment and mode of practice thereof, I carry out my invention in part by supporting a properly-tensioned circular saw blade in a horizontal position, at two points on opposite sides of the center of the blade and lying on a first diametral axis thereof. The blade is then elastically deflected by pressing it vertically upwardly against reaction forces acting on opposite sides of the center of the blade at points lying along a second diametral axis preferably perpendicular to the first. This tends to warp the blade into the form of a saddle, i.e. a form in which sections of the blade parallel to the first diametral axis are upwardly concave, while sections parallel to the second diametral axis tend to become upwardly convex.

A model properly-tensioned blade, when not deflected by externally-applied forces other than gravity, tends to assume an upwardly concave cross-section when held horizontally; in terms of art, the center of the blade is said to drop through, and the blade is said to be loose in the center. This means that the blade material toward the center is very slightly stretched or elongated relative to that toward the periphery of the blade, so that the dimension of the blade measured along its surface is slightly greater than the outside diameter, and the blade tends to spring into an arcuate cross-section, or to oil-can. This may occur in either direction along the major rotational axis while the blade is at rest, and is determined by the effect of gravity when the blade is horizontal.

This loose-center condition is necessary to make a blade of any substantial size run straight and true at cutting speeds. The centrifugal force applied to any element of the blade is equal to $MV^2/R$, or in terms of angular velocity, $M\omega^2 R$, where M is the mass of the element, R is its radius, and V and $\omega$ are its linear and angular velocities, respectively. As M and $\omega$ are constants throughout the blade, the centrifugal force and stress acting on any element increases in direct proportion to the radius; therefore, the strain increases from the center toward the periphery, and the loose-center blade stretches into a flat condition when rotating at cutting speed.

The consequence is that, when a properly-tensioned blade is deflected according to my method, the tendency of the blade to become upwardly convex along the second diametral axis is opposed by the tendency of the loose center to drop through into an upwardly concave form. I utilize this opposition by limiting the upward and downward deflections of the blade at such relative values that these tendencies just counterbalance one another in a region of the blade lying along the second diametral axis. As a result, a radius of the blade surface in this region becomes substantially flat or rectilinear.

Having determined the correct deflections for producing this condition in a blade known to be properly tensioned, I substitute in its place any selected blade of the same specifications, whose unknown state of tension is to be determined and corrected, and apply the same elastic deflections in the same relative locations, directions, and values as before. I then pass a position-detecting device through a horizontal plane and substantially along a radius of the blade surface coinciding with the second diametral axis of deflection. Any detected deviation of the blade surface upwardly from the correct rectilinear locus previously determined for the properly-tensioned blade indicates a region of excessive tension, and is therefore taken as a signal to designate that region for correction, that is, for loosening by appropriate hammering. Deviations of the surface below the correct locus reflect relatively loose spots of lower tension, which do not require any corrective response, but are left to be automatically compensated for by the loosening of the relatively tight or high-tension regions.

As the detection process is carried out, the blade is rotated around its center relative to the first and second diametral axes of deflection, which are fixed; thus substantially the entire blade surface is progressively inspected, and tight spots are either corrected by immediate hammering, or marked for later hammering. The blade is then turned over, and the process repeated on the reverse surface. The result is to correct both local regions of excess tension, and to conform the overall tension distribution of the selected blade to that of the properly-tensioned blade.

In addition to the simplicity of the mechanism required for carrying out this process, there are other inherent advantages. It is a simple matter to convert from one blade thickness, diameter, or degree of overall tension to another. Apart from a readjustment of the relative heights of the blade-deflecting members with an appropriate model blade, the first of these conversions requires no change but to note a new reference height on the dial indicator; the second only an adjustment of the radial locations of the deflecting members; and the third calls for no other changes.

I have also observed that the improved method is effective to detect and correct a peculiar condition known as twist, encountered in a certain proportion of saw blades, more adequately than my aforementioned patented methods. Twist is a condition that can best be demonstrated by grasping a flexible disc at opposite ends of a diameter, and applying clockwise and counterclockwise twisting moments to the opposite edges of the disc. It is not yet clear to me why the new method is more effective to correct this condition, but the result has been clearly established in practice.

DESCRIPTION OF THE PREFERRED EMBODIMENT

Figure 1:
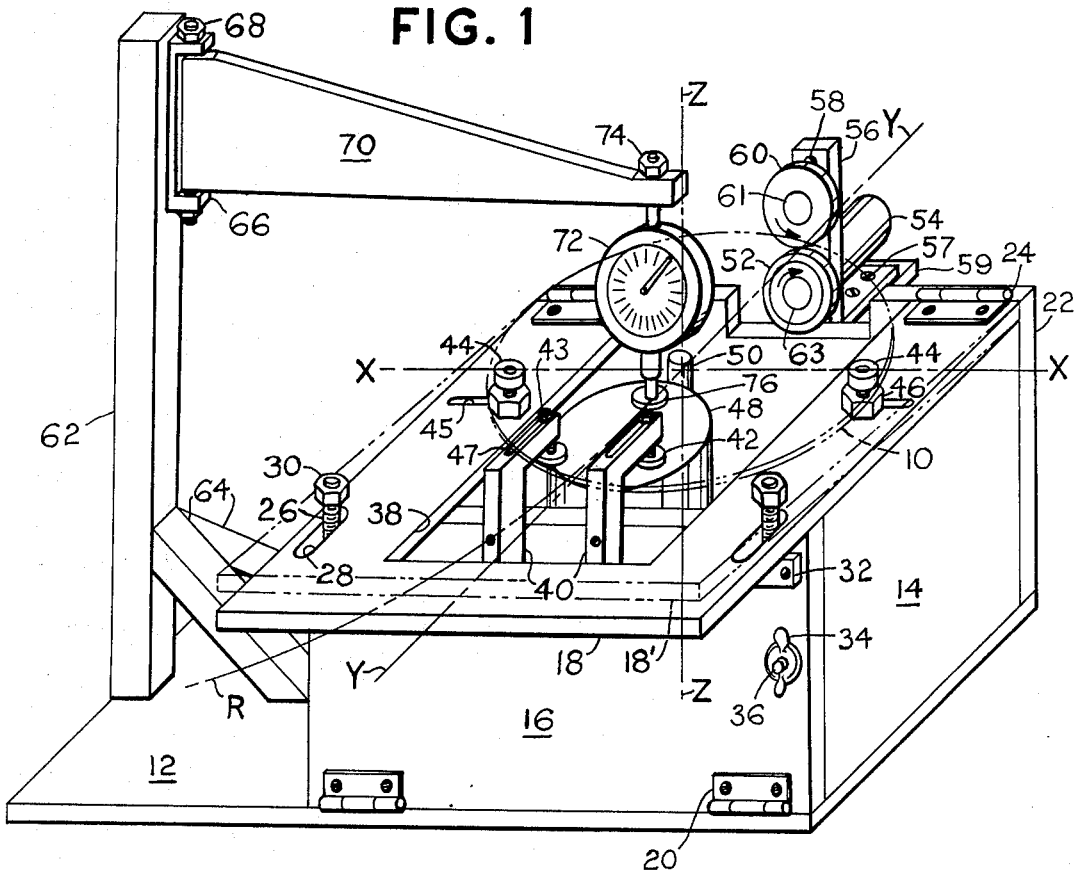
FIG. 1 is a pictorial view of a preferred embodiment of the improved saw blade tension-detecting machine.

Referring to FIG. 1, a preferred embodiment of the improved saw tensioning machine is organized about a base plate 12, and includes a pair of side plates 14 and a back plate 22 secured to the base plate, and a front plate 16 pivotally secured to the base plate by hinges 20. Resting on these plates is a top plate 18 having a U-shaped recess 38, and pivotally secured to the back plate 22 by hinges 24 so that it may be raised manually from the position shown in full lines to a dotted line position 18'. The limit of this upward motion is determined by a pair of stop nuts 30 adjustably threaded on studs 26, which are mounted on the front plate 16 by means of blocks 32, and extend upwardly through elongated slots 28 in the top plate to permit the front plate 16 to be swung forwardly about the hinges 20 to a limited extent. The front plate is normally held in the illustrated position by a wing nut 34 threaded on a stud 36 fixed to the side plate 14, but may be released by removing the wing nut, and swung forwardly to permit a circular saw blade 10 to be inserted in or removed from the machine.

Mounted in elongated slots 45 in the top plate 18 are a pair of support screws 44 threaded in the top plate, and locked in place by nuts 46. The screws 44 are aligned on a horizontal axis X—X passing through a fixed center post 50, which is receivable through the center hole of the circular saw blade 10 to locate the blade for rotational movement, but permits the blade to move freely in a vertical direction. The axis X—X thus constitutes a first diametral axis of the saw blade.

Means are provided for pressing the saw blade downwardly along a second diametral axis Y—Y, perpendicular to the X—X axis, thereby to elastically deflect the blade into the form of a saddle. These means include a pair of L-shaped brackets 40 attached to the front plate 16. A pair of threaded pressure feet 42 are received through elongated slots 47 in the brackets 40, and are locked in horizontally and vertically adjusted positions by pairs of nuts 43. It is preferred to employ two of the pressure feet 42, symmetrically spaced on either side of the Y—Y axis, rather than one foot aligned on this axis, in order to provide convenient access to a portion of the blade lying along the Y—Y axis for inspection and subsequent hammering. However, it will be apparent that the resultant of the downward force applied by the symmetrically-spaced pressure feet 42 will be aligned on the Y—Y axis.

At the opposite periphery of the saw blade, a rotatable wheel 60 also acts to press downwardly on the blade on the Y—Y axis. The vertical height of this roller may be adjusted by moving its axle 61 in an elongated slot 58 formed in an L-shaped supporting bracket 56, the axle being secured in adjusted position by a nut (not shown) threaded thereon and engaging the rear surface of the bracket. A rubber-rimmed roller 52 has its axle 63 rotatably supported in the bracket 56 and drivingly connected with a suitable electric motor 54. The axle 61 is adjusted to engage a saw blade 10 of any specified thickness against the roller 52. The motor 54 is thus operable to cause the rollers to rotate in directions shown by the arrows, and thereby turn the saw blade about the center post 50.

The bracket 56 bearing the rollers 52 and 60 and the motor 54 is mounted by threaded fasteners 57 in elongated slots (not shown) formed in a mounting pad 59 which is attached to the back plate 22 and extends rearwardly therefrom. This permits the rollers 52 and 60 to be adjusted along the Y—Y axis together with the pressure feet 42, while the support screws 44 are adjusted along the X—X axis, to accommodate saw blades of various diameters. These elements are so adjusted that the saw blade is engaged near its periphery, but not so close as to interfere with its cutting edges or gullets.

In the lowered position of the top plate shown at 18, the support screws 44 and pressure feet 42 are so adjusted with respect to the roller 60 as to lie near or on the surface of the blade 10, so that the blade rotates in a flat undeflected form. However, by manually raising the top plate to the dotted line position 18', the support screws 44 are raised to cooperate with the pressure feet 42 and the roller 60 to deflect the saw blade into a saddle-shaped configuration; that is to say, sections of the blade parallel to the axis Y—Y become upwardly convex, while sections parallel to the X—X axis assume an upwardly concave form. The appropriate adjustments will be further explained after the principles of the invention are discussed.

The configuration of the blade surface along a radius extending from the center post 50 toward the pressure feet 42, and approximately aligned along the Y—Y axis, is then detected by means of the contact foot 76 of a conventional dial indicator 72. This indicator is mounted by a nut 74 on an arm 70 that is pivotally movable in a horizontal plane about a pair of pivot points 68 mounted in a bracket 66, which is in turn supported by a post 62 attached to the base plate 12 and firmly supported by braces 64. In operation, the arm 70 is swung manually to pass the contact foot 76 along a horizontal arc R to detect the vertical position of the surface of the saw blade, and may be swung completely away from the blade to permit access for manual hammering along the Y—Y axis.

A massive anvil 48 is supported on the base plate 12 under the saw blade, and has a horizontal top surface against which the blade lies when the top plate 18 is lowered to the full-line position. The operation of the machine of FIG. 1 will be further explained after the following description of FIGS. 2-5, which illustrate the principles of the invention.

It should be emphasized that the blade curvatures shown in FIGS. 2-5 are greatly exaggerated for the sake of clarity. The actual deflections of blades of ordinary size are on the order of only a few thousandths of an inch, and would not be visible to the eye.

Figure 2:
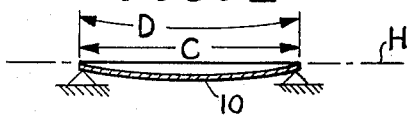
FIG. 2 is a cross-section illustrating the behavior of a properly-tensioned saw blade when supported at its periphery in a stationary horizontal position.

FIG. 2 illustrates a cross-section of a properly-tensioned saw blade 10 stationarily supported in a horizontal positon so that its periphery lies in a horizontal plane H. A correctly tensioned blade is loose in the center, as previously explained, so that the center drops through and causes the blade to assume an upwardly concave configuration. The stretching or elongation of the center of the blade with respect to its peripheral portion is reflected in the fact that the dimension D, measured on the arcuate surface of the blade, is slightly greater than the outside diameter C. However, when such a blade is rotated at cutting speed, the differential centrifugal forces that have previously been outlined stretch the blade into a flat configuration that cuts straight and true.

Figure 3:
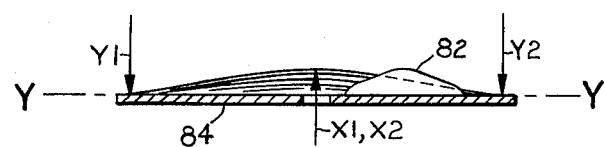
FIG. 3 is a cross-sectional view of a properly-tensioned saw blade when deflected in accordance with the improved method.
Figure 4:
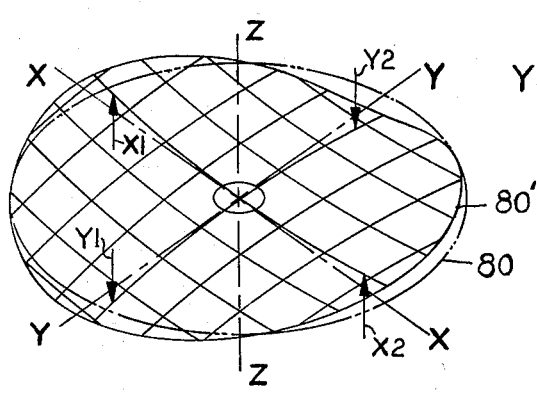
FIG. 4 is an isometric view illustrating the saddle form of a normally-flat, untensioned saw blade when deflected in the same manner as the blade of FIG. 3.
Figure 5:
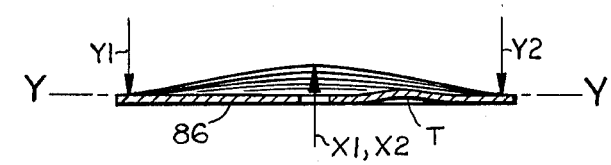
FIG. 5 is a cross-sectional view of an improperly-tensioned saw blade deflected in the same manner as the blade of FIG. 3, but showing the effect of a local region of excess tension.

The pressure feet 42 and the roller 60 of FIG. 1 apply downward deflecting forces on the Y—Y axis, illustrated at Y1 and Y2 in FIGS. 3-5, while the support screws 44 apply opposed forces X1 and X2 along the X—X axis. The amount of deflection is determined by the amount of elevation of the scews 44 when the top plate is raised to the position 18', and this is adjusted by means of the nuts 30. FIG. 4 illustrates at 80' the saddle shape that the machine would apply to an untensioned normally-flat blade 80, i.e. a blade which would be substantially flat when supported as in FIG. 2, but for a slight sag due solely to its weight. A series of intersections with the blade surface of planes parallel to the X-Z and Y-Z axes are shown to clarify the nature of the compound curvature.

The tendency of a properly-tensioned blade that is loose in the center to assume an upwardly-concave configuration, as shown in FIG. 2, counteracts the tendency of the blade to become upwardly convex along the axis Y—Y under the bending moments applied by the forces X1-X2 and Y1-Y2. According to my method, the elevation of the top plate at 18' is adjusted by the stop nuts 30 until a condition is reached in which these tendencies are in balance, and a radius of a properly-tensioned deflected blade 84 in FIG. 3 is substantially flat and rectilinear along the Y—Y axis. This is illustrated by a straight-edge 82 resting flat on the surface of the blade. In contrast, it may be noted that the deflecting forces X1 and X2 applied by the support screws 44 are added to the tendency of the loose center to produce concavity along the X—X axis, so that the blade surface assumes a more pronounced upwardly concave form in that direction. It may also be noted that one of the two deflecting forces Y1 or Y2 is divided by its application through the separated pressure feet 42, but nevertheless produces a resultant downward deflecting force which acts effectively on the Y—Y axis. The separation of the pressure feet lends convenience to the use of the dial indicator 72, and also permits ready access to the blade for hammering to correct tension defects. The result is the same as if a single pressure foot 42 were applied on the Y—Y axis, except that the specified flatness on the radius of the blade extending between the pressure feet may be attained while an opposite radius extending to the roller 60 remains very slightly convex. However, since the detecting and hammering operations are carried out entirely on the radius extending between the pressure feet, this does not create any practical difficulty.

The method is carried out by first mounting a properly-tensioned model blade in the machine, and swinging the arm 70 inwardly to position the dial indicator 72 over the blade surface. The top plate 18 is then raised to 18', against the stop nuts 30, lifting the support screws 44 to deflect the blade against the pressure feet 42 and the roller 60. The blade is turned slowly, manually or by the motor 54, and the arm 70 is moved across the blade surface to determine its configuration. The relative heights of the screws 44, pressure feet 42, and roller 60 are adjusted by means of the stop nuts 30, until the dial indicator 72 discloses that the condition illustrated in FIG. 3 has been attained.

The properly-tensioned model blade is removed from the machine after lowering the top plate 18, swinging the arm 70 out from the blade, unscrewing the wing nut 34, and swinging the front plate 16 forwardly to clear the pressure feet 42 from the blade surface. Any selected similar blade of unknown tension can then be treated by placing it on the center post 50, closing the front plate 16, replacing the wing nut 34 on the stud 36, and repeating the detecting steps previously carried out on the model blade. Supposing that points elevated from the previously determined flat locus are discovered, they represent regions of excess tension which should be designated for hammering to loosen them. The rotation of the blade is stopped when such a region is located, and it is either hammered at that time, or suitably marked for a later hammering operation. FIG.

5 illustrates the cross-sectional configuration of a blade 86 which has a general a proper tension distribution, but which has such a region of excess tension T projecting upwardly from the Y—Y axis. This is shown on a highly exaggerated scale for clarity; such regions actually project from the surrounding surface to a height measured in thousandths of an inch.

What I claim is:

1. The method of detecting the tension in a circular saw blade which comprises the steps of:

supporting the blade horizontally;

elastically deflecting the blade by pressing it vertically at points on opposite sides of the center of the blade and defining a first diametral axis of the blade, against opposed vertical resultant forces acting on opposite sides of the center of the blade at further points circumferentially spaced apart from said first diametral axis and defining a second diametral axis, whereby warping the blade into a saddle form with an upper surface of the blade being concave along said first diametral axis and tending toward upward convexity along said second diametral axis, said tendency toward upward convexity being offset by and to the extent of any tendency of the central portion of the horizontally-supported blade to drop through in the presence of a decreasing level of tension from the periphery of the blade toward its center;

while detecting any convexity of a portion of said upper surface of the blade lying along said second diametral axis, as an indication of the relative levels of tension existing diametrally across the blade.

2. The method recited in claim 1, together with the further step, carried out concurrently with said detecting step, of turning said blade around a major rotational axis thereof passing through the center of the blade and mutually perpendicular to said first and second diametral axes.

3. The method of detecting the levels of local and overall tension in a selected circular saw blade which deviate from those in a properly-tensioned normal blade having a substantially uniform level of tension circumferentially, and a decreasing level of tension radially inwardly from the perimeter to the center thereof, which comprises the steps of:

applying first and second opposed elastic deflections to said normal blade in opposite directions parallel to a major rotational axis thereof to distort said blade into the form of a saddle, while supporting said normal blade horizontally, said first deflection applying a first bending moment tending to deflect said normal blade into an upwardly concave curvature along a first diametral axis thereof, said second deflection applying a second bending moment tending to deflect said normal blade in an upwardly convex curvature along a second diametral axis thereof substantially perpendicular to said first diametral axis;

limiting said deflections at values such that the tendency of said radially-inwardly decreasing tension to produce an upwardly concave curvature of said normal blade counterbalances the tendency of said second bending moment to produce an upwardly convex curvature, and causes a radius of said normal blade lying along said second diametral axis to assume a substantially rectilinear configuration;

applying said first and second opposed elastic deflections to said selected blade substantially in the same relative locations, directions and values as they were applied to said normal blade in the preceding steps;

rotating said selected blade around the major rotational axis thereof with respect to said first and second diametral axes;

while detecting deviations from rectilinearity and toward upward convexity of a radius of said selected blade lying along said second diametral axis;

and designating any local regions of said selected blade found by said detecting step to be upwardly convex, as regions requiring reduction of local tension to conform the tension distribution of said selected blade substantially to that of said normal blade.

4. A machine for detecting the levels of local and overall tension in a selected saw blade relative to those in a properly-tensioned model saw blade having a substantially uniform level of tension circumferentially, and a decreasing level of tension radially inwardly from the perimeter to the center thereof, said machine comprising:

means for supporting a saw blade horizontally;

first and second means for applying opposed elastic deflections parallel to a major rotational axis of said blade to distort said blade into the form of a saddle, said first deflection means being constructed and arranged to apply a first bending moment tending to deflect said blade into an upwardly concave curvature along a first diametral axis thereof, said second deflection means being constructed and arranged to apply a second bending moment tending to deflect said blade into an upwardly convex curvature along a second diametral axis thereof substantially peripendicular to said first diametral axis;

adjustable stop means cooperating with said first and second deflection means to limit said deflections at adjusted values;

said machine being constructed and arranged to apply said adjusted values of deflection to said selected or model blades interchangeably.

5. A machine as recited in claim 4, together with means for detecting the height of the surface of a blade deflected by said machine along said second diametral axis.

6. A machine as recited in claim 4, together with means for turning a blade deflected by said machine about said major rotational axis with respect to said first and second diametral axes.

7. A machine for detecting the tension in a saw blade, comprising:

means for supporting the blade horizontally at least at two points on opposite sides of the center of the blade, said points defining a first diametral axis of the blade;

means for resisting upward movement of the blade at at least two further points on opposite sides of the center of the blade, said further points defining a second diametral axis of the blade circumferentially spaced from said first diametral axis;

means for elastically deflecting the blade by pressing said supporting means and said resisting means in opposite directions along a major rotational axis of the blade normal to said first and second diametral axes, thereby to deflect the blade into a saddle form with an upper surface of the blade being concave along said first diametral axis and tending toward upward convexity along said second diametral axis, said tendency toward upward convexity being offset by and to the extent of any tendency of the central portion of the horizontally-supported blade to drop through in the presence of a decreasing level of tension from the periphery of the blade toward its center;

and means for detecting any convexity of a portion of said upper surface of the blade lying along said second diametral axis, as an indication of the relative levels of tension existing diametrally across the blade.

* * * * *